United States Patent [19]

Downey et al.

[11] Patent Number: 5,466,382

[45] Date of Patent: Nov. 14, 1995

[54] SYNERGISTIC MICROBICIDAL COMBINATIONS CONTAINING 4,5-DICHLORO-2-N-OCTYL-3-ISOTHIAZOLONE AND CERTAIN COMMERCIAL BIOCIDES

[75] Inventors: Angela B. Downey, Lansdale; Valerie S. Frazier, Wyndmoor; Gary L. Willingham, Glenside, all of Pa.

[73] Assignee: Rohm and Haas Company, Philadelphia, Pa.

[21] Appl. No.: 237,538

[22] Filed: May 3, 1994

[51] Int. Cl.⁶ ................................................. A61K 31/425
[52] U.S. Cl. .................... 210/764; 106/18.21; 106/18.22; 405/211; 405/216; 514/241; 514/245; 514/372; 514/600
[58] Field of Search ...................... 514/372, 600, 514/245, 241; 210/764; 405/211, 216; 106/18.21, 18.22

[56] References Cited

U.S. PATENT DOCUMENTS

| | | | |
|---|---|---|---|
| 3,761,488 | 9/1973 | Lewis et al. | 260/302 |
| 4,105,431 | 8/1978 | Lewis et al. | 71/67 |
| 4,252,694 | 2/1981 | Lewis et al. | 252/545 |
| 4,265,899 | 5/1981 | Lewis et al. | 424/270 |
| 4,279,762 | 7/1981 | Lewis et al. | 252/47 |
| 4,964,892 | 10/1990 | Hsu | 71/67 |
| 4,990,525 | 2/1991 | Hsu | 514/372 |
| 5,236,888 | 8/1993 | Hsu | 504/154 |
| 5,292,763 | 3/1994 | Hsu | 514/372 |
| 5,334,389 | 8/1994 | Gerhart | 424/409 |

*Primary Examiner*—Neil McCarthy
*Attorney, Agent, or Firm*—Michael B. Fein

[57] ABSTRACT

Synergistic microbicidal compositions are disclosed, comprising 4,5-dichloro-2-n-octyl-3-isothiazolone and one or more known microbicides for more effective, and broader control of microorganisms in various systems.

13 Claims, No Drawings

SYNERGISTIC MICROBICIDAL COMBINATIONS CONTAINING 4,5-DICHLORO-2-N-OCTYL-3-ISOTHIAZOLONE AND CERTAIN COMMERCIAL BIOCIDES

BACKGROUND OF THE INVENTION

1. Field of the Invention

This invention relates to biocides which are especially useful for marine, industrial and architectural coatings.

2. Prior Art

Isothiazolones are described in U.S. Pat. Nos. 3,761,488; 4,105,431; 4,252,694; 4,265,899 and 4,279,762, and elsewhere. Their use as microbicides is well known.

Isothiazolones act synergistically with certain other active ingredients, see e.g. U.S. Pat. Nos. 4,990,525; 4,964,892; 5,236,888; and 5,292,763.

4,5-Dichloro-2-n-octyl-3-isothiazolone is a special species of isothiazolone which has utility in marine, industrial and architectural coatings. Isothiazolones are known skin sensitizers. The use of isothiazolones in certain coating applications is limited because the level of isothiazolone required for effective control of microbial growth is higher than the recommended exposure limit to avoid sensitization.

SUMMARY OF THE INVENTION

The term "microbicidal" (or "antimicrobial" or "biocidal") as used herein is intended to encompass, but is not restricted to, all bactericidal, fungicidal and algicidal activity.

It is therefore an object of the invention to provide microbicidal compositions of 4,5-dichloro-2-n-octyl-3-isothiazolone which provide effective control of microbial growth and have reduced skin sensitization potential.

This object, and others which will become apparent from the following disclosure, is achieved by the present invention which comprises in one aspect compositions formed from 4,5-dichloro-2-n-octyl-3-isothiazolone and one or more of a second component selected from the group consisting of 2-methylthio-4-tert-butylamino- 6-cyclopropylamino-s-triazine and N,N-dimethyl-N'-phenyl-(N'-fluorodichloromethylthio)-sulfamide. These compositions unexpectedly afford synergistic antimicrobial activity against a wide range of microorganisms: the disruptive action on the microorganisms by the two compounds together is unexpectedly greater than the sum of both compounds taken alone.

DETAILED DESCRIPTION AND THE PREFERRED EMBODIMENT

The synergy demonstrated in the compositions of the invention does not arise from the expected activity of the components nor from the expected improvement in activity. As a result of the synergy, the effective dose required can be lowered, which is not only more economical but also increases safety margins. The synergistic compositions of the present invention provide more effective and broader control of microorganisms in a number of systems.

The present invention thus provides a composition having microbicidal activity which includes 4,5-dichloro-2-n-octyl-3-isothiazolone and a second component selected from one or more of the group consisting of: 2-methylthio-4-tert-butylamino- 6-cyclopropylamino-s-triazine and N,N-dimethyl-N'-phenyl-(N'-fluorodichloromethylthio)-sulfamide; wherein the weight ratio of 4,5-dichloro-2-n-octyl-3-isothiazolone to the second component is from about 60:1 to about 1:500.

Important applications of the synergistic antimicrobial compositions of the present invention include but are not limited to: inhibiting the growth of hard and soft marine fouling organisms, such as algae, tunicates, hydroids, bivalves, bryozoans, polychaete worms, sponges, and barnacles, on submerged structures, such as underwater surfaces of ships, piers, docks, pilings, fishnets, heat exchangers, dams, and piping structures, such as intake screens; inhibiting the growth of algae, bacteria and fungi in industrial coatings, such as paints, elastomeric coatings, mastics, adhesives, sealants, and caulks; wood treatments, such as pressure or vacuum impregnation or anti-sapstain treatments; controlling slime-producing algae, bacteria and fungi in pulp and papermills and cooling towers; latex emulsions, and joint cements; preserving cutting fluids; as a spray or dip treatment for textiles and leather to prevent mold growth; protecting paint films, especially exterior paints, from attack by algae which occurs during weathering of the paint film; protecting processing equipment from slime deposits during manufacture of cane and beet sugar; preventing microorganism buildup and deposits in air washer or scrubber systems and in industrial fresh water supply systems; preserving fuel; controlling microorganism contamination and deposits in oil field drilling fluids and muds, and in secondary petroleum recovery processes; preventing bacterial and fungal growth in paper coatings and coating processes; controlling bacterial and fungal growth and deposits during the manufacture of various specialty boards, e.g., cardboard and particle board; controlling bacterial and fungal growth in clay and pigment slurries of various types; as a hard surface disinfectant to prevent growth of bacteria and fungi on walls, floors, etc.; as a preservative for cosmetic and toiletry raw materials, floor polishes, fabric softeners, household and industrial cleaners; in swimming pools to prevent algae growth; inhibiting the growth of harmful bacteria, yeasts, fungi on plants, trees, fruits, seeds, or soil; preserving agricultural formulations, electrodeposition systems, diagnostic and reagent products, medical devices; protecting animal dip compositions against the buildup of microorganisms, and in photoprocessing to prevent buildup of microorganisms, and the like.

The compositions of the invention may be added separately to any system or may be formulated as a simple mixture comprising its essential ingredients, and if desired a suitable carrier or solvent, or as an aqueous emulsion or dispersion.

The invention also provides a method of inhibiting the growth of bacteria, fungi or algae in a locus subject to contamination by bacteria, fungi or algae, which comprises incorporating into or onto the locus in an amount which is effective to adversely affect the growth of bacteria, fungi or algae any of the compositions defined above.

The composition of the invention can be formulated as a solution in a wide range of organic solvents. The solutions generally contain about 5 to 30% by weight of the active composition. It is generally more convenient to provide the compositions in a water-diluted form: this may be accomplished by adding an emulsifier to the organic solution followed by dilution with water, or by formulating as a dispersible solid.

The composition of the invention can also be added to a decorative, industrial or marine coating composition further comprising a film forming polymer. When used for decorative or industrial coating compositions, the active composition can be anywhere from about 0.05 to 2.0% by weight of the coating composition. When used for marine coating compositions, the active composition can be anywhere from about 0.5 to 15.0% by weight of the coating composition.

By decorative coatings is meant paint, sealants, and varnishes. By industrial coating is meant paints, elastomeric coatings, mastics, adhesives, sealants, and caulks. By marine coating is meant a coating applied to or on submergible structures, such as underwater surfaces of ships, piers, docks, pilings, fishnets, heat exchangers, dams, and piping structures, such as intake screens.

In general, the weight ratio of 4,5-dichloro-2-n-octyl-3-isothiazolone to second component in the composition may be in the range of from about 60:1 to about 1:500. The other specific and preferred ratios are given in the examples.

EXAMPLE 1

The synergism of two-component compositions is demonstrated by testing a wide range of concentrations and ratios of compounds against a marine alga, *Enteromorpha intestinalis* (UTEX 739), and a marine diatom, *Achnanthes brevipes* (UTEX 2077). Vertical and horizontal concentration ladders of two compounds are created in a 96-well microtiter plate in synthetic sea water medium. Thus, each concentration in one ladder is tested against every concentration in the other ladder. Each test plate also includes a concentration ladder of each compound alone. *A. brevipes*, a single celled organism, was vortexed to blend, quantitated spectrophotometrically, and then standardized to an absorbance of 0.14 at 660 nm by adjusting the sample by adding either more synthetic sea water or more organism. The *E. intestinalis* inoculum was quantified by fluorometric assay of a chlorophyll a extraction of the culture, a commonly used and accepted method described by Lobban, C. S.; Chapman, D. J. and Kremer, B. P. in "Experimental Phycology, A Laboratory Manual," (1988, Cambridge University Press). The inoculum extraction was assayed and compared to a standard curve developed using chlorophyll a (C-1644) (obtainable from Sigma Chemical Co., PO Box 14508, St. Louis, Mo. 63178) and the inoculum adjusted to reach a final concentration of 0.01 ppm chlorophyll a per milliliter of inoculum.

Synthetic sea water can be prepared by dissolving 40 g of synthetic sea salt (available as an enriched blend of synthetic sea salt crystals developed for use in home aquaria, such as Reef Crystals, from Aquarium Systems, 8141 Tyler Blvd., Mentor, Ohio 44060) in one liter of deionized water. The salinity of the synthetic sea water is adjusted to a reading of 1.0021 on a Sea Test specific gravity meter by adding more water or synthetic sea salt. To this solution are then added 0.092 g of Guillard's (f/2) Marine Enrichment Basal Salt Mixture (G-1775) (available from Sigma Chemical Co., PO Box 14508, St. Louis, Mo. 63178), sufficient selenious acid to reach a final concentration of $10^{-8}M$, sufficient nickel sulfate to reach a final concentration of $10^{-8}M$, sufficient sodium orthovanadate to reach a final concentration of $10^{-8}M$, and sufficient potassium chromate to reach a final concentration of $10^{-9}M$.

The lowest concentrations of each compound to inhibit visible growth at 25° after 21 days were taken as the minimum inhibitory concentration (MIC). The MIC were taken as end points of activity. End points for the mixtures of compound A (4,5 dichloro-2-octyl-3-isothiazolone) and compound B (second component microbicide) were then compared with the end points for the isothiazolone A alone and compound B alone. Synergism was determined by a commonly used and accepted method described by Kull, F. C.; Eisman, P. C.; Sylwestrowicz, H. D. and Mayer, R. L., in applied Microbiology 9:538–541 (1961) using the ratio determined by $$Qa/QA + Qb/QB = Synergy\ Index(SI)$$

wherein

QA=concentration of compound A in parts per million (ppm), acting alone, which produced an end point.

Qa=concentration of compound A in ppm, in the mixture, which produced an end point.

QB=concentration of compound B in ppm, acting alone, which produced an end point.

Qb=concentration of compound B in ppm, in the mixture, which produced an end point.

When the sum of Qa/QA and Qb/QB is greater than one, antagonism is indicated. When the sum is equal to one additivity is indicated, and when less than one synergism is demonstrated.

The test results for demonstration of synergism of microbicide combinations are shown in Tables 1 and 2. Each table concerns the combination of 4,5-dichloro-2-octyl- 3-isothiazolone and one other microbicide, and shows:

1. the identity of the second microbicide (compound B);
2. test against *Enteromorpha intestinalis* (E. intest) and *Achnanthes brevipes* (A. brev);
3. the end-point activity in ppm measured by MIC for either compound alone or their combinations;
4. the synergy index (SI) based on the above formula;
5. the weight ratios for synergism. It will be appreciated by those skilled in the art that the ratios given are approximate only.

The MIC values of each compound tested alone (QA or QB) are end-point activities. Replicate synergy tests were conducted on A. brev. These results are reported in Tables 1 and 2.

TABLE 1

| | End-point Activity in ppm | | | |
|---|---|---|---|---|
| Organism | Compound A | Compound B-1 | SI | A:B-1 |
| E. intest | 1.5 (MIC) | — | | |
| | 0.8 | 02 | 1.03 | 4:1 |
| | 0.8 | 0.1 | 0.78 | 8:1 |
| | 0.8 | 0.05 | 0.66 | 16:1 |
| | — | 0.4 (MIC) | | |
| A. brev | 3 (MIC) | — | | |
| | 0.75 | 0.75 | 0.75 | 1:1 |
| | 0.75 | 0.4 | 0.52 | 2:1 |
| | 1.5 | 0.2 | 0.63 | 7.5:1 |
| | 1.5 | 0.1 | 0.57 | 15:1 |
| | — | 1.5 (MIC) | | |
| | 6 (MIC) | — | | |
| | 1.5 | 0.2 | 0.75 | 7.5:1 |
| | — | 0.4 (MIC) | | |
| | 6 (MIC) | — | | |
| | 3 | 0.1 | 0.57 | 30:1 |
| | 3 | 0.05 | 0.53 | 60:1 |
| | — | 1.5 (MIC) | | |
| | 6 (MIC) | — | | |
| | 3 | 0.05 | 0.75 | 60:1 |
| | — | 0.2 (MIC) | | |

Compound A = 4,5-dichloro-2-n-octyl-3-isothiazolone
Compound B-1 = 2-methylthio-4-tert-butylamino-6-cyclopropylamino-s-triazine Synergistic ratios of compound A:compound B-1 range from 60:1 to 1:1.

TABLE 2

End-point Activity in ppm

| Organism | Compound A | Compound B-2 | SI | A:B-2 |
|---|---|---|---|---|
| A. brev | 6 (MIC) | — | | |
| | 1.5 | 50 | 0.75 | 1:33 |
| | 3 | 25 | 0.75 | 1:8 |
| | 3 | 12.5 | 0.625 | 1:4 |
| | 3 | 6 | 0.56 | 1:2 |
| | 1.5 | 25 | 0.75 | 1:17 |
| | 1.5 | 12.5 | 0.5 | 1:8 |
| | — | 100 (MIC) | | |
| | 3 (MIC) | — | | |
| | 0.75 | 25 | 0.75 | 1:33 |
| | — | 50 (MIC) | | |

Compound A = 4,5-dichloro-2-n-octyl-3-isothiazolone
Compound B-2 = N,N-dimethyl-N'-phenyl-(N'-fluorodichloromethylthio)-sulfamide Synergistic ratios of compound A:compound B-2 range from 1:2 to 1:33.

As can be seen by review of Tables 1 and 2, the compositions of the invention demonstrate synergistic microbicidal activity as measured by MIC and show surprisingly greater activity than the algebraic sum of the individual components which make up each composition.

EXAMPLE 2

A synergy study was conducted on Artemia salina. Stock solutions of 4,5-dichloro-2-n-octyl-3-isothiazolone (Compound A) and 2-methylthio-4-tert-butylamino-6-cyclopropylamino-s-triazine (Compound B-1) were prepared in dimethyl formamide (DMF) at 80 ppm for Compound A and at 10,000 ppm for Compound B-1.

Artemia eggs were hatched overnight at 25° C. in Instant Ocean (IO) artificial sea water which was vigorously aerated, Hatched nauplii were separated from unhatched eggs and transferred to a tank containing IO with an aeration block at 25° C. for 24 hours. The concentration of Artemia was adjusted as closely as possible to 50 Artemia per 10 ml. Aliquots (10 ml) were pipetted into glass tubes which were dosed with 10 μl of one of the biocide stock solutions. Controls were dosed with 10 μl DMF.

The tubes were incubated at 25° C. for 24 hours and the number of dead Artemia recorded. Dead Artemia sink to the bottom of the tube and are easily counted under a binocular microscope. The Artemia were considered dead when no movement was observed during a two-second period when viewed under the microscope. The number of live Artemia were calculated after counting the total number of Artemia in the tube after the addition of a few drops of fixative. In practice, tubes in which 1–2 Artemia (<5%) survived were recorded as exhibiting 100% mortality. Mortality in controls was typically 5–10% (i.e. 2–5 dead Artemia per tube). If mortality in controls was >15%, the test was rejected.

The percent mortality in each of three replicate controls was determined and the mean percent control mortality ($P_C$) was calculated. The percent mortality for each replicate ($P_O$) was also determined. The corrected percent mortality ($P_T$) for each replicate was then calculated using the following formula:

$$P_T = \frac{P_O - P_C}{100 - P_C} \times 100$$

The mean percent mortality for each amount of biocide was determined from the $P_T$'s for three replicates. The mean percent mortalities for Compound A alone and Compound B-1 alone are reported in Table 3.

TABLE 3

Mean Percent Mortality of Artemia for Compounds A and B

| Compound A (ppm) | Compound B-1 (ppm) | Mean % Mortality |
|---|---|---|
| 0.02 | — | 0 |
| 0.04 | — | 18.3 |
| 0.06 | — | 59.7 |
| 0.08 | — | 86.3 |
| — | 0.02 | 2.3 |
| — | 0.04 | 0 |
| — | 0.06 | 2.7 |
| — | 0.08 | 2.3 |
| — | 0.1 | 5.0 |
| — | 1.0 | 2.3 |
| — | 10.0 | 5.7 |

Compound A = 4,5-dichloro-2-n-octyl-3-isothiazolone
Compound B-1 = 2-methylthio-4-tert-butylamino-6-cyclopropylamino-s-triazine For the synergism tests, the above procedure was repeated except that both Compound A and Compound B-1 were each added to the samples in 10 μl DMF. Thus, controls and individually dosed samples contained 20 μl DMF. The concentrations of Compound A used were 0.02, 0.04, 0.06, and 0.08 ppm. The concentrations of Compound B-1 used were the same as those of Compound A plus 0.1, 1.0, and 10.0 ppm.

The $P_T$ for each replicate of the combinations was calculated and the mean percent mortality for the combinations was determined from the $P_T$'s for three replicates. This observed mean percent mortality for the combination was compared to the sum of the mean percent mortalities (expected mean percent mortalities) for the individual compounds. If the observed mean percent mortality of the combination was higher than the expected mean percent mortalities of the individual compounds, then the combination was synergistic. These results are reported in Table 4.

TABLE 4

Mean Percent Mortality of Artemia for Combinations of Compounds A and B-1

| Compound A (ppm) | Compound B-1 (ppm) | A:B-1 | Expected % Mortality | Observed % Mortality |
|---|---|---|---|---|
| 0.02 | 0.02 | 1:1 | 2.3 | 1.7 |
| 0.02 | 0.1 | 1:5 | 5.0 | 1.7 |
| 0.02 | 1.0 | 1:50 | 2.3 | 16.3 |
| 0.02 | 10.0 | 1:500 | 5.7 | 26.3 |
| 0.04 | 0.04 | 1:1 | 18.3 | 31.7 |
| 0.04 | 0.1 | 1:2.5 | 23.3 | 32.7 |
| 0.04 | 1.0 | 1:25 | 20.6 | 45.3 |
| 0.04 | 10.0 | 1:250 | 24.0 | 51.7 |
| 0.06 | 0.06 | 1:1 | 62.4 | 64.7 |
| 0.06 | 0.1 | 1:1.7 | 64.7 | 58.7 |
| 0.06 | 1.0 | 1:17 | 62.0 | 82.0 |
| 0.06 | 10.0 | 1:170 | 65.4 | 86.7 |
| 0.08 | 0.08 | 1:1 | 88.6 | 95.7 |
| 0.08 | 0.1 | 1:1.25 | 91.3 | 94.0 |
| 0.08 | 1.0 | 1:12.5 | 88.6 | 100 |
| 0.08 | 10.0 | 1:125 | 92.0 | 100 |

Compound A = 4,5-dichloro-2-n-octyl-3-isothiazolone
Compound B-1 = 2-methylthio-4-tert-butylamino-6-cyclopropylamino-s-triazine From the above data it can be seen that the synergistic ratios of Compound A:Compound B-1 range from 1:1 to 1:500.

EXAMPLE 3

Synergy studies were conducted on three fungi; *Aspergillus niger* (ATCC 6275), *Cladosporium cladosporides* (ATCC 16022), and *Penicillium purpurogenum* (ATCC 52427); with 4,5-dichloro-2-n-octyl-3-isothiazolone and N,N-dimethyl-N'-phenyl-(N'-fluorodichloromethylthio)sulfamide. The fungi were grown on Potato dextrose agar and incubated for 5 days at 30° C. The fungi were washed with 50 ppm of Triton X-100 in water and then filtered through 4 layers of sterile cheese cloth. The fungi were then standardized to $10^6$ spores/ml using a hemocytometer slide.

The synergy studies were conducted using microtiter plate assays in Potato dextrose broth medium. In this method, a wide range of concentrations was tested by preparing two-fold serial dilutions of the compounds in 96-well plastic microtiter plates. All liquid media transfers were performed with calibrated single or multichannel digital pipetters. Stock solutions of compounds were prepared in appropriate solvents and dispensed to the growth medium. All subsequent dilutions in plates were made using the desired growth medium; total volume of liquid in each well was 100 µl. Each plate contained a concentration of both compounds made by serially titrating equal volumes of liquids in two directions in the microtiter plate. Each plate contained a control row for each combination (one component only), hence, the individual compound MIC values were also determined.

The results for the synergy tests are reported in Table 5.

TABLE 5

| Organism | End-point Activity in ppm | | SI | A:B-2 |
|---|---|---|---|---|
| | Compound A | Compound B-2 | | |
| *Aspergillus niger* | 6 (MIC) | — | | |
| | 3 | 2 | 0.52 | 1.5:1 |
| | 0.8 | 63 | 0.62 | 1:79 |
| | — | 125 (MIC) | | |
| | 12 (MIC) | — | | |
| | 6 | 0.63 | 0.50 | 10:1 |
| | 0.8 | 45 | 0.56 | 1:56 |
| | — | 90 (MIC) | | |
| *Cladosporium cladosporides* | 12 (MIC) | — | | |
| | 6 | 4 | 0.56 | 1.5:1 |
| | 3 | 32 | 0.75 | 1:10 |
| | — | 63 (MIC) | | |
| | 12 (MIC) | — | | |
| | 6 | 8 | 0.56 | 1:1.3 |
| | 0.8 | 63 | 0.56 | 1:79 |
| | — | 125 (MIC) | | |
| *Penicillium purpurogenum* | 6 (MIC) | — | | |
| | 3 | 4 | 0.56 | 1:1.3 |
| | 3 | 16 | 0.75 | 1:5 |
| | — | 63 (MIC) | | |
| | 12 (MIC) | — | | |
| | 6 | 0.5 | 0.52 | 12:1 |
| | 0.8 | 16 | 0.56 | 1:20 |
| | — | 32 (MIC) | | |

Compound A = 4,5-dichloro-2-n-octyl-3-isothiazolone
Compound B-2 = N,N-dimethyl-N'-phenyl-(N'-fluorodichloromethylthio)sulfamide Synergistic ratios of compound A:compound B-2 range from 12:1 to 1:79.

The synergistic activities of the compositions of the invention are applicable to algae, bacteria, fungi, fouling organisms, and mixtures thereof. Thus, the combinations not only lowers the use-level of biocide but also broadens the spectrum of activity. This is especially useful in situations where either component alone does not achieve the best results due to weak activity against certain organisms.

What is claimed is:

1. A composition comprising at least two components the first component of which is 4,5-dichloro-2-n-octyl-3-isothiazolone and the second component of which is selected from one or more of the following compounds: 2-methylthio-4-tert-butylamino-6-cyclopropylamino-s-triazine and N,N-dimethyl-N'-phenyl-(N'-fluorodichloromethylthio)sulfamide; wherein the first component and second component act synergistically with each other and are present in a weight ratio of first component to second component is in the range of from about 60:1 to about 1:500.

2. The composition of claim 1, wherein the ratio of the first component to the second component, 2-methylthio-4-tert-butylamino-6-cyclopropylamino-s-triazine, is in the range of from about 2:1 to about 60:1.

3. The composition of claim 1, wherein the ratio of the first component to the second component, N,N-dimethyl-N'-phenyl-(N'-fluorodichloromethylthio)sulfamide, is in the range of from about 12:1 to about 1:79.

4. The composition of claim 1, wherein the ratio of the first component to the second component, N,N-dimethyl-N'-phenyl-(N'-fluorodichloromethylthio)sulfamide, is in the range of from about 1:4 to about 1:8.

5. A composition according to claim 1, further comprising an emulsifier and water.

6. A composition according to claim 1 in the form of a coating which comprises film forming polymer.

7. A composition according to claim 1 further including film forming polymer, said composition being in the form of a paint, elastomeric coating, mastic, adhesive, sealant, caulk, or varnish.

8. A method of protecting a marine or freshwater structure against fouling by marine or freshwater organisms comprising applying a composition according to claim 1.

9. A method for inhibiting the growth of bacteria, fungi, or algae in a locus subject to contamination by bacteria, fungi, or algae, which comprises incorporating onto or into the locus, in an amount which is effective to adversely affect the growth of bacteria, fungi, or algae, a composition according to claim 1.

10. The method of claim 9 wherein the locus is an aqueous medium, and the composition additionally contains an emulsifier and water.

11. The method of claim 9 wherein the locus is wood.

12. A method of protecting a marine or freshwater structure against fouling by marine or freshwater organisms comprising applying a coating composition according to claim 6.

13. A method of protecting a marine or freshwater structure against fouling by marine or freshwater organisms comprising applying a composition according to claim 1.

* * * * *